(12) United States Patent
Sato

(10) Patent No.: US 8,992,429 B2
(45) Date of Patent: Mar. 31, 2015

(54) ULTRASONIC DIAGNOSTIC APPARATUS

(75) Inventor: Takeshi Sato, Nasushiobara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 1512 days.

(21) Appl. No.: 12/023,515

(22) Filed: Jan. 31, 2008

(65) Prior Publication Data

US 2008/0188751 A1 Aug. 7, 2008

(30) Foreign Application Priority Data

Feb. 5, 2007 (JP) ................... 2007-025922

(51) Int. Cl.
*A61B 8/00* (2006.01)
*G01S 15/89* (2006.01)
*G01S 7/52* (2006.01)
*A61B 8/06* (2006.01)
*A61B 8/13* (2006.01)

(52) U.S. Cl.
CPC ............ *G01S 15/8981* (2013.01); *A61B 8/06* (2013.01); *A61B 8/13* (2013.01); *G01S 7/52077* (2013.01)
USPC .......................................... 600/454; 600/453

(58) Field of Classification Search
USPC .......... 600/437, 453, 454, 458, 459, 455, 457
See application file for complete search history.

(56) References Cited

U.S. PATENT DOCUMENTS

| | | |
|---|---|---|
| 5,349,524 A | 9/1994 | Daft et al. |
| 6,390,980 B1 | 5/2002 | Peterson et al. |
| 2005/0080329 A1* | 4/2005 | Uchibori ............... 600/407 |
| 2005/0148875 A1* | 7/2005 | Sato ..................... 600/453 |
| 2007/0078347 A1* | 4/2007 | Srinivasan et al. ....... 600/465 |

FOREIGN PATENT DOCUMENTS

| | | |
|---|---|---|
| JP | 10-99333 | 4/1998 |
| JP | 11-267125 | 10/1999 |
| JP | 2005-312773 | 11/2005 |

OTHER PUBLICATIONS

English Translation of JP 2005-312773 (Sato) provided by IPDL tool.*

* cited by examiner

*Primary Examiner* — Katherine Fernandez
(74) *Attorney, Agent, or Firm* — Oblon, McClelland, Maier & Neustadt, L.L.P.

(57) ABSTRACT

An ultrasonic diagnostic apparatus has an IQ signal acquiring unit, a signal generating unit, a first Doppler signal extracting unit and a second Doppler signal extracting unit. The IQ signal acquiring unit acquires a plurality of groups including an ultrasonic reception IQ signal, under respective interference conditions that differ from one another. The signal generating unit generates an added signal by adding the groups, and to generate an added amplitude signal by adding the amplitudes of the groups. The first Doppler signal extracting unit extracts a first Doppler signal that corresponds to motion from the added signal. The second Doppler signal extracting unit configured to extract a second Doppler signal having a property that differ from the property of the first Doppler signal. At this point, the Doppler signal extracting units are configured so as to extract the Doppler signals respectively while reducing an artifact due to tissue motion.

7 Claims, 10 Drawing Sheets

US 8,992,429 B2

ULTRASONIC DIAGNOSTIC APPARATUS

BACKGROUND OF THE INVENTION

1. Field of the Invention

The present invention relates to a color Doppler ultrasonic diagnostic apparatus which visualizes a blood flow utilizing Doppler signals acquired by transmitting/receiving ultrasonic waves, and in particular to an ultrasonic diagnostic apparatus having a function of reducing motion artifacts occurring due to changes in a speckle pattern that correspond to a motion of a tissue.

2. Description of the Related Art

In an ultrasonic color Doppler method, ultrasonic waves are transmitted/received to/from an object, and the Doppler signal that corresponds to the blood flow, which is a component of an ultrasonic echo signal occurring in the object, is two-dimensionally displayed. The ultrasonic echo signal acquired from the object is a convoluted signal, in which the signal from the tissue is convoluted with a blood flow signal that is the Doppler signal that results from the blood flow. Accordingly, an MIT (moving target indication) filter (which is also referred to as a "wall filter") is used which is based on the fact that the motion velocity of the tissue is slow, thereby suppressing a clutter signal which is the Doppler signal from the tissue.

However, in a case in which there is a large amount of tissue motion due to breathing or a beating of the heart, an amplitude of the speckle pattern changes. Here, the speckle pattern is a granular pattern occurring due to a random interference of ultrasonic waves. Accordingly, the clutter signal cannot be sufficiently suppressed using only the MTI filter having a function of a suppressing signal under fixed conditions. As a result, such an arrangement has a problem of color artifacts which are referred to as "motion artifacts".

In order to reduce the motion artifacts, a method has been proposed, in which the motion velocity of the tissue (clutter velocity) is calculated, and a phase correction is performed for the Doppler signal of an original signal, or properties of the MTI filters are adjusted (for example, see Japanese Unexamined Patent Application publication No. 10-99333, Japanese Unexamined Patent Application publication No. 11-267125, U.S. Pat. No. 5,349,524 specification).

The aforementioned method in which the clutter velocity is calculated and phase correction is performed for the original signal is an effective method without adverse effects as long as the phase correction is performed for the Doppler signal from a heart or a large blood vessel. However, the motion artifacts cannot be sufficiently suppressed by only the phase correction performed for the Doppler signal. In order to solve this problem, a technique has been proposed in which additional adjustments are made to a cut-off frequency of the MTI filters.

Also, a technique has been proposed in which processing is performed utilizing the baseband (IQ) signal generated in a reception circuit of the ultrasonic diagnostic apparatus, and the amplitude thereof, which is equivalent processing to the instantaneous clutter velocity correction processing (for example, see Japanese Unexamined Patent Application publication No. 2005-312773).

With the aforementioned conventional processing, the cut-off frequency is increased according to an increase in the clutter velocity. However, in some cases, such conventional processing with settings that are sufficient to ensure that the motion artifacts are suppressed has a problem that the blood flow signal is removed. Accordingly, such processing for adjusting the cut-off frequency of the MTI filters is not actively employed. Accordingly, in this situation, it is difficult for the ultrasonic color Doppler method to sufficiently remove the motion artifacts occurring due to the tissue motion.

SUMMARY OF THE INVENTION

The present invention has taken into consideration the above-described problems and it is an object of the present invention to provide an ultrasonic diagnostic apparatus which can reduce motion artifacts occurring due to changes in the speckle pattern that correspond to the motion of the tissue, while evading an occurrence of adverse effects that the blood flow signal are removed.

To solve the above-described problems, the present invention provides the ultrasonic diagnostic apparatus, comprising: an IQ signal acquiring unit configured to acquire a plurality of groups including an ultrasonic reception IQ signal, under respective interference conditions that differ from one another; a signal generating unit configured to generate an added signal by adding the groups, and to generate an added amplitude signal by adding the amplitudes of the groups; a first Doppler signal extracting unit configured to extract a first Doppler signal that corresponds to motion from the added signal; and a second Doppler signal extracting unit configured to extract a second Doppler signal having a property that differ from the property of the first Doppler signal, wherein the first Doppler signal extracting unit and the second Doppler signal extracting unit are configured so as to extract the first Doppler signal and the second Doppler signal respectively while reducing an artifact due to tissue motion.

To solve the above-described problems, the present invention provides the ultrasonic diagnostic apparatus, comprising: an IQ signal acquiring unit configured to acquire a plurality of groups including an ultrasonic reception IQ signal, under respective interference conditions that differ from one another; a Doppler signal detecting unit configured to detect a plurality of groups including a Doppler signal based on the groups including the ultrasonic reception IQ signal in every group; and an estimating unit configured to calculate based on the groups including a Doppler signal at least one of groups including a self-correlation function, groups including a blood flow velocity, and groups including a variance in the blood flow, and groups including a blood flow power signal in every group, and to estimate at least one of a single blood flow velocity, a single blood flow variance, and a single blood flow power signal by performing an addition or a weighting addition of the calculation results thus calculated.

To solve the above-described problems, the present invention provides the ultrasonic diagnostic apparatus, comprising: an IQ signal acquiring unit configured to acquire a plurality of groups including an ultrasonic reception IQ signal, under respective interference conditions that differ from one another; a Doppler signal detecting unit configured to detect a plurality of groups including a Doppler signal based on the groups including the ultrasonic reception IQ signal in every group; and an estimating unit configured to estimate a blood flow signal to be output based on the groups including the Doppler signal.

DESCRIPTION OF THE PREFERRED EMBODIMENTS

Description will be made regarding an ultrasonic diagnostic apparatus according to an embodiment of the present invention with reference to the accompanying drawings.

Figure 1:
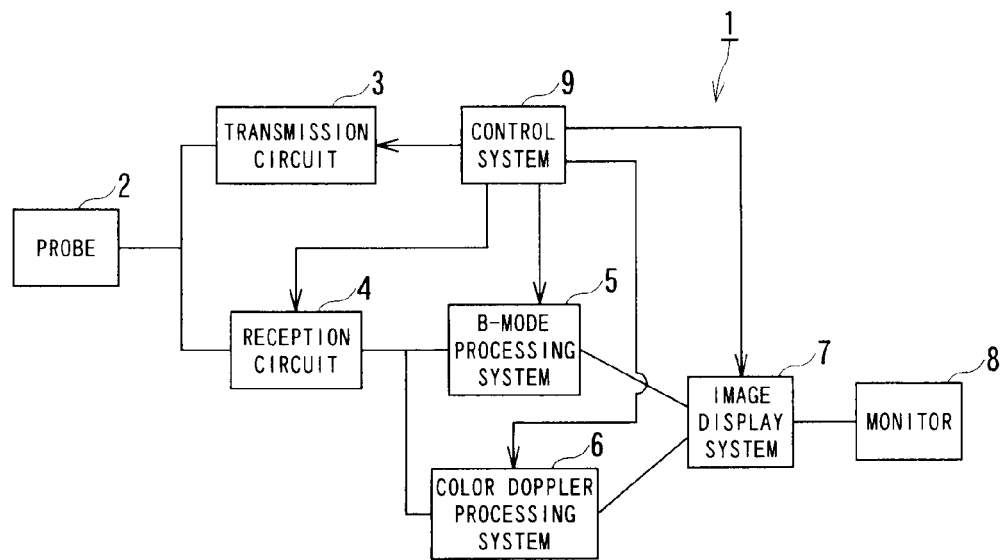
FIG. 1 is a block diagram which shows an ultrasonic diagnostic apparatus according to a first embodiment of the present invention.

FIG. 1 is a block diagram which shows an ultrasonic diagnostic apparatus according to a first embodiment of the present invention.

The ultrasonic diagnostic apparatus 1 has a probe 2, a transmission circuit 3, a reception circuit 4, a B-mode processing system 5, a color Doppler processing system 6, an image display system 7, a monitor 8, and a control system 9.

The transmission circuit 3 has a function of applying transmission signals to multiple ultrasonic oscillators included within the probe 2 with predetermined delay times so as to form an ultrasonic transmission beam.

The probe 2 including the multiple ultrasonic oscillators has a function of transmitting, to the interior of an object (not shown), transmission signals applied by the transmission circuit 3 in the form of an ultrasonic signal. Furthermore, the probe 2 has a function of receiving ultrasonic echo signals from within the object, and outputting the signals thus received to the reception circuit 4 in the form of an electric signal.

The reception circuit 4 includes a digital beam former which performs phasing addition of N-channel received signals that correspond to the respective ultrasonic oscillators. Using the digital beam former, the reception circuit 4 performs phasing addition of received signals that correspond to the multiple ultrasonic oscillators. Such an arrangement provides a function of generating a baseband signal (IQ signal) in the baseband range, and a function of outputting the IQ signal thus generated to the B-mode processing system 5 and the color Doppler processing system 6. The reception circuit 4 has a configuration for performing the phasing addition processing for the received N-channel signals. With such an arrangement, the received N-channel signals are divided into a first block consisting of a first channel signal to an N/2'th channel signal and a second block consisting of an (N/2+1)'th channel signal to an N'th channel signal. Then, the phasing addition is separately performed for the first block and the second block. With such an arrangement, the reception circuit 4 outputs an IQ signal IQ1, which is obtained by performing the phasing addition processing for the received signals that belong to the first block consisting of the first channel signal to the N/2'th channel signal, and an IQ signal IQ2, which is obtained by performing the phasing addition processing for the received signals that belong to the second block consisting of the (N/2+1)'th channel signal to the N'th channel signal.

The B-mode processing system 5 has a function of generating B-mode data based on the IQ signal acquired from the reception circuit 4, and a function of outputting the B-mode data thus generated to the image display system 7. The color Doppler processing system 6 has a function of generating color Doppler data based on the IQ signal acquired from the reception circuit 4, and a function of outputting the color Doppler data thus generated to the image display system 7.

The image display system 7 has a function of generating display image data and a function of outputting the display image data thus generated to the monitor 8. With such an arrangement, the image display system 7 performs coordinate transformation for the B-mode data acquired from the B-mode processing system 5 and the color Doppler data acquired from the color Doppler processing system 6, and generates a composite image thereof, thereby generating the display image data.

The control system 9 has a function of transmitting control signals to the transmission circuit 3, the reception circuit 4, the B-mode processing system 5, the color Doppler processing system 6, and the image display system 7, thereby centrally controlling these components.

Figure 2:
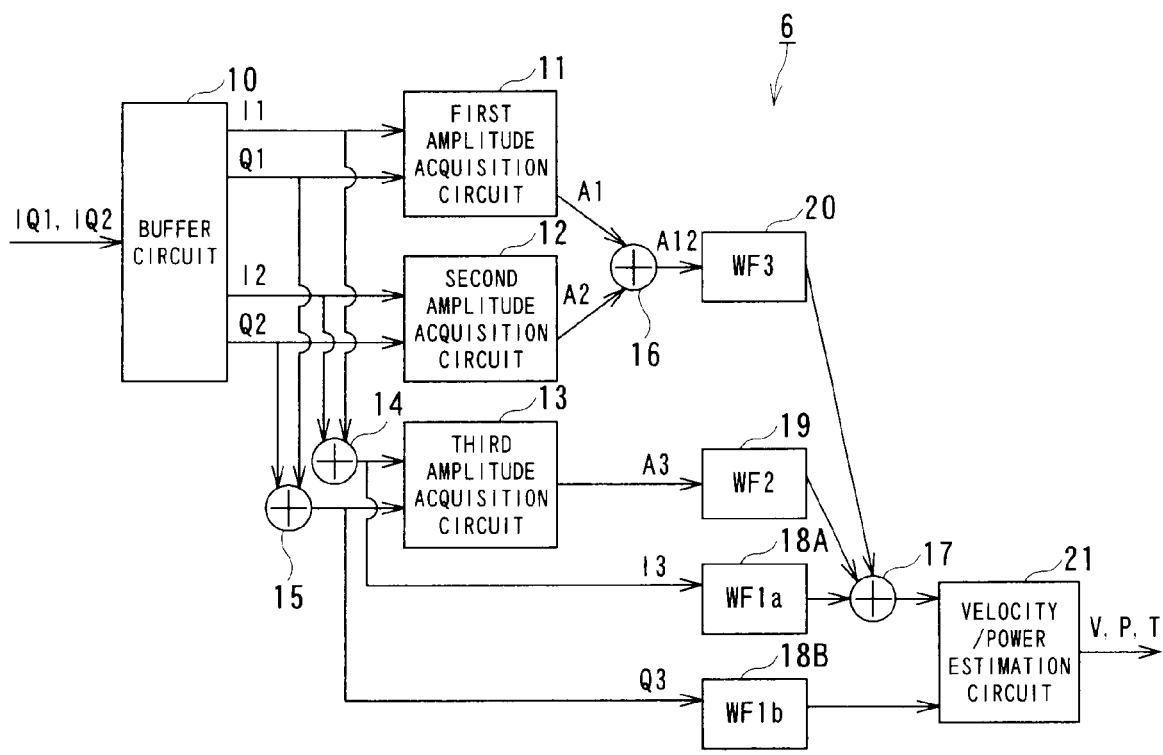
FIG. 2 is a block diagram which shows a detailed configuration of a color Doppler processing system shown in FIG. 1.

FIG. 2 is a block diagram which shows a detailed configuration of the color Doppler processing system 6 shown in FIG. 1.

The color Doppler processing system 6 has a buffer circuit 10, a first amplitude acquisition circuit 11, a second amplitude acquisition circuit 12, a third amplitude acquisition circuit 13, a first adder 14, a second adder 15, a third adder 16, a fourth adder 17, two first MTI filters (WF1a, WF1b) 18A and 18B, a second MTI filter (WF2) 19, a third MTI filter (WF3) 20, and a velocity/power estimation circuit 21.

The buffer circuit 10 is connected to the output side of the reception circuit 4. The units connected to the output side of the buffer circuit 10 are the first amplitude acquisition circuit 11, the second amplitude acquisition circuit 12, the first adder 14, and the second adder 15. The third adder 16 is connected as a common component to the output sides of the first amplitude acquisition circuit 11 and the second amplitude acquisition circuit 12. The output sides of the first adder 14 and the second adder 15 are connected to the MTI filters (WF1a and WF1b) 18A and 18B, respectively. Furthermore, the output side of the third amplitude acquisition circuit 13 is connected to the second MTI filter (WF2) 19. The output side of the third adder 16 is connected to the third MTI filter (WF3) 20. Moreover, the fourth adder 17 is connected to the output side of the first MTI filter (WF1a) 18A connected to the output side of the first adder 14, and the output sides of the second MTI filter (Wf2) 19 and the third MTI filter (WF3) 20. The velocity/power estimation circuit 21 is connected as a common component to the output side of the first MTI filter (WF1b) 18B connected to the output side of the second adder 15 and the output side of the fourth adder 17. Furthermore, the output side of the velocity/power estimation circuit 21 is connected to the image display system 7, which is a downstream system.

The buffer circuit 10 has a function of writing, in the depth (distance) direction, multiple IQ signals IQ1 and IQ2, which have been sequentially acquired from the reception circuit 4, thereby storing the IQ signals. Furthermore, the buffer circuit has a function of reading out the IQ signals IQ1 and IQ2 along the packet direction, which have been stored at the same depth (position), and a function of outputting the IQ signals IQ1 and IQ2 thus read out to the first amplitude acquisition circuit 11, the second amplitude acquisition circuit 12, and the first adder 14 or the second adder 15.

Figure 3:
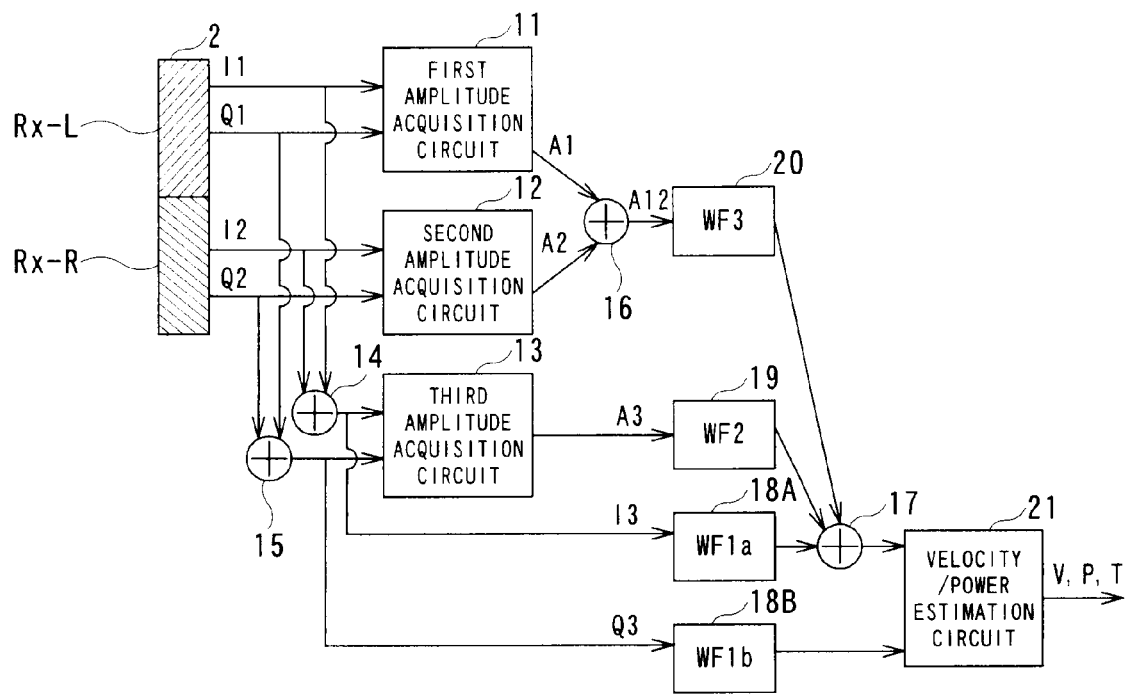
FIG. 3 is a diagram which shows a relation among IQ signals generated in an arrangement in which a reception opening of a probe shown in FIG. 1 is divided into a first block consisting of a first channel to the N/2'th channel and a second block consisting of a (N/2+1)'th channel to a N'th channel.

FIG. 3 is a diagram which shows the relation among the IQ signals generated in an arrangement in which the reception opening of the probe 2 shown in FIG. 1 is divided into a first block consisting of the first channel to the N/2'th channel and a second block consisting of the (N/2+1)'th channel to the N'th channel.

As shown in FIG. 3, the IQ signals IQ1, which correspond to the first channel to the N/2'th channel, are generated based on the received signals received by the first block Rx-L of the probe 2. Furthermore, the IQ signals IQ2, which correspond to the (N/2+1)'th to the N'th channel, are generated based on the received signals received by the second block Rx-R of the probe 2. Then, the IQ signals IQ1, which correspond to the first channel to the N/2'th channel, are output to the first amplitude acquisition circuit 11, and the IQ signals IQ2, which correspond to the (N/2+1)'ch to the N'th channel, are output to the second amplitude acquisition circuit 12.

Furthermore, I (real) signals, i.e., the I signals I1 that are components of the IQ signals IQ1, which correspond to the first channel to the N/2'th channel, and the I signals I2 that are components of the IQ signals IQ2, which correspond to the (N/2+1)'th to the N'th channel, are output to the first adder 14. On the other hand, the Q (img) signals, i.e., the Q signals Q1 that are components of the IQ signals IQ1, which correspond to the first channel to the N/2'th channel, and the Q signals Q2 that are components of the IQ signals IQ2, which correspond to the (N/2+1)'th to the N'th channel, are output to the second adder 15.

Each of the first amplitude acquisition circuit 11, the second amplitude acquisition circuit 12, and the third amplitude acquisition circuit 13 has a function of acquiring the amplitude of the corresponding input signal, and a function of outputting the amplitude signal. Furthermore, each of the first adder 14, the second adder 15, the third adder 16, and the fourth adder 17 has a function of adding multiple input signals and outputting the signal thus added.

The properties of the third MTI filter (WF3) 20 are adjusted so as to allow the signal components of the input signal ranging from a predetermined frequency f1 to a frequency f2 that is higher than the frequency f1 to pass through the filter. The properties of the second MTI filter (WF2) 19 are adjusted so as to allow the signal components of the input signal ranging up to a frequency f3 that is higher than the frequency f2 to pass through the filter. The properties of the first MTI filters (FW1a and FW1b) 18A and 18B are adjusted so as to allow the signal components of the input signal that are equal to or higher than the frequency f3 to pass through the filter. Accordingly, the signal components of the input signal that are equal to or lower than the predetermined frequency f1 are cut off by each of the first MTI filters (FW1a and FW1b) 18A and 18B, the second MTI filter (WF2) 19, and the third MTI filter (WF3) 20.

The velocity/power estimation circuit 21 has a function of estimating a velocity, a variance, and a power of the blood flow based on the input signals, and a function of outputting the velocity, the variance, and the power of the blood flow thus estimated to the image display system 7, which is a downstream system, in the form of the velocity signal V, the variance signal T, and the power signal P, respectively.

Next, description will be made regarding the operations and functions of the ultrasonic diagnostic apparatus 1.

Upon the transmission circuit 3 receiving a transmission signal application instruction from the control system 9, the transmission circuit 3 repeatedly applies transmission signals to the corresponding multiple ultrasonic oscillators included within the probe 2 with predetermined delay times that correspond to the depth of the focus position and the transmission direction of the ultrasonic transmission beam. Each of the oscillators transmits the transmission signals, which are sequentially applied by the transmission circuit 3, to the interior of the object in the form of an ultrasonic signal. Thus, the ultrasonic echo signals occurring at each position within the object are sequentially received by the N-channel ultrasonic oscillators, and are output to the reception circuit 4 as received signals in the form of electric signals.

As described above, the received signals which are used for generating the B-mode data for displaying a cross-sectional image of the object and the received signals used for generating the color Doppler data for displaying the blood flow information with respect to the object are sequentially output to the reception circuit 4 multiple times in a predetermined order. That is to say, with such an arrangement, the focus position of the ultrasonic transmission beam is changed so as to sequentially receive the received signals from within the object in a predetermined range of transmission directions and depths. The received signals thus acquired are output to the reception circuit 4. Here, the received signal to be used for generating the color Doppler data is acquired for each sampling point, along the same transmission direction and at the same depth, a predetermined number of times corresponding to the ensemble number.

The digital beam former included in the reception circuit 4 performs phasing addition of the received signals which have been received by the ultrasonic oscillators that belong to the first block consisting of the first channel to the N/2'th channel and which are to be used for generating the color Doppler data, thereby generating the IQ signals IQ1. Furthermore, phasing addition is performed for the received signals which have been received by the ultrasonic oscillators that belong to the second block consisting of the (N/2+1)'th channel to the N'th channel and which are to be used for generating the color Doppler data, thereby generating the IQ signals IQ2. These two kinds of IQ signals, i.e., IQ1 and IQ2, which correspond to the respective positions within the object, are output to the color Doppler processing system 6. Furthermore, for the received signals to be used for generating the B-mode data, the digital beam former performs phasing addition processing for all the received signals which correspond to the first channel to the N'th channel. The IQ signals thus generated are output to the B-mode processing system 5.

The B-mode processing system 5 performs data processing for the IQ signals to be used for generating the B-mode data, thereby generating the B-mode data. The B-mode data thus generated is output to the image display system 7.

On the other hand, the color Doppler processing system 6 generates the color Doppler data based on the two kinds of IQ signals, i.e., IQ1 and IQ2, and outputs the color Doppler data thus generated to the image display system 7. Specifically, the two kinds of IQ signals IQ1 and IQ2 acquired for each transmission direction and depth in the form of time series data are temporarily stored in the buffer circuit 10. Then, the predetermined ensemble number of IQ signals IQ1, which correspond to the same transmission direction and the same depth and which correspond to the first channel to the N/2'th channel, are read out along the packet direction, and the IQ signals IQ1 thus read out are sequentially output to the first amplitude acquisition circuit 11. In addition, the predetermined ensemble number of IQ signals IQ2, which correspond to the same transmission direction and the same depth and which correspond to the (N/2+1)'th channel to the N'th channel, are read out along the packet direction, and the IQ signals IQ2 thus read out are sequentially output to the second amplitude acquisition circuit 12.

The first amplitude acquisition circuit 11 acquires the amplitudes of the IQ signals IQ1, and outputs the amplitudes thus acquired to the third adder 16 as the amplitude signals A1. The second amplitude acquisition circuit 12 acquires the amplitudes of the IQ signals IQ2, and outputs the amplitudes thus acquired to the third adder 16 as the amplitude signals A2. The third adder 16 adds these two kinds of amplitude signals A1 and A2, thereby generating the added signal A12. The added signal A12 thus generated is output to the third MTI filter (WF3) 20.

On the other hand, the I signals I1 included in the IQ signals IQ1 that correspond to the first channel to the N/2'th cannel and the I signals I2 included in the IQ signals IQ2 that correspond to the (N/2+1)'th channel to the N'th channel are output to the first adder 14. Furthermore, the Q signals Q1 included in the IQ signals IQ1 that correspond to the first channel to the N/2'th cannel and the Q signals Q2 included in the IQ signals IQ2 that correspond to the (N/2+1)'th channel to the N'th channel are output to the second adder 15.

The first adder 14 adds these two kinds of I signals, i.e., I1 and I2, thereby generated the I signal I3. The I signal I3 thus generated is output to the third amplitude acquisition circuit 13 and one of the first MTI filters, i.e., the first MTI filter (Wf1a) 18A. The second adder 15 adds the two kinds of Q signals, i.e., Q1 and Q2, thereby generating the Q signal Q3.

The Q signal Q3 thus generated is output to the third amplitude acquisition circuit 13 and the other first MTI filter, i.e., the first MTI filter (Wf1b) 18B.

The I signal I3 to be input to the first MTI filter (WF1a) 18A is a signal obtained by adding the I signals I1 that correspond to the first channel to the N/2'th channel and the I signals I2 that correspond to the (N/2+1)'th channel to the N'th channel. Accordingly, the I signal I3 is equivalent to the ordinary I signal which is obtained via the first channel to the N'th channel, i.e., via the entire opening. In the same way, the Q signal Q3 to be output to the first MTI filter (WF1b) 18B is equivalent to the ordinary Q signal which is obtained via the entire opening.

The third amplitude acquisition circuit 13 acquires the amplitude of the IQ signal IQ3 consisting of the I signal I3 and the Q signal Q3 acquired from the first adder 14 and the second adder 15, and outputs the amplitude thus acquired to the second MTI filter (WF2) 19 as the amplitude signal A3. The IQ signal IQ3 is equivalent to the ordinary IQ signal IQ which is obtained via the entire opening. Accordingly, the amplitude signal A3 input to the second MTI filter (WF2) 19 is also equivalent to the amplitude signal A of the ordinary IQ signal IQ obtained via the entire opening.

That is to say, the aforementioned four kinds of signals, i.e., the I signal I3 and the Q signal Q3 obtained by simply adding the pair of IQ signals IQ1 and IQ2 that have been subjected to phasing addition after signal acquisition via the two partitions of the opening, the amplitude signal A3 of the IQ signal IQ3, and the added signal A12 obtained by adding the respective amplitude signals A1 and A2 of the pair of IQ signals IQ1 and IQ2, are subjected to filtering processing using the two first MTI filters (WF1a, WF1b) 18A and 18B, the second MTI filter (WF2) 19, and the third MTI filter (WF3) 20, respectively.

As described above, the properties of the first MTI filters (WF1a, WF1b) 18A and 18B are set so as to allow the signal components of the input signal with frequencies that are equal to or higher than the frequency f3 to pass through the filter. The properties of the second MTI filter (WF2) 19 are set so as to allow the signal components of the input signal ranging from the frequency f2 to the frequency f3 to pass through the filter. The properties of the third MTI filter (WF3) 20 are set so as to allow the signal components of the input signal ranging from the frequency f1 to the frequency f2 to pass through the filter. Here, the frequency is not restricted to the frequency employed in the ordinary Fourier theory. Rather, the frequency as used here should be interpreted in the broad sense to include the calculation results obtained by polynomial orthogonal transformation.

Let us consider an arrangement in which the number of input signals, i.e., the ensemble numbers, is 16 for each of the first MTI filters (WF1a, WF1b) 18A and 18B, the second MTI filter (WF2) 19, and the third MTI filter (WF3) 20. With such an arrangement, the weight E1 to be applied to the first MTI filters (WF1a, WF1b) 18A and 18B with respect to the polynomial orthogonal space may be set to one represented by a following equation (1-1). The weight E2 to be applied to the second MTI filter (WF2) 19 may be set to one represented by a following equation (1-2) with respect to the polynomial orthogonal space. The weight E3 to be applied to the third MTI filter (WF3) 20 may be set to one represented by a following equation (1-3) with respect to the polynomial orthogonal space.

$$E1=[0,0,0,0,0,0,0,0,0,1,1,1,1,1,1,1] \quad (1\text{-}1)$$

$$E2=[0,0,0,0,0,0,1,1,0,0,0,0,0,0,0,0] \quad (1\text{-}2)$$

$$E2=[0,0,0,0,1,1,0,0,0,0,0,0,0,0,0,0] \quad (1\text{-}3)$$

It should be noted that, in the equation (1-1), (1-2), and (1-3), the element value at the far left inside the square brackets represents the zero-order (DC: Direct Current) coefficient, and as the values advance to the right, the order of the coefficient represented by the element value increases by 1.

Then, the fourth adder 17 adds the output signals output from the first MTI filter (WF1*a*) 18A for the I signal I3, the second MTI filter (WF2) 19, and the third MTI filter (WF3) 20, which have the aforementioned properties. The output signal of the fourth adder 17 and the output signal of the first MTI filter (WF1*b*) 18B for the Q signal Q3 are input to the velocity/power estimation circuit 21.

The velocity/power estimation circuit 21 obtains the power signal P by adding the output signal of the fourth adder 17 and the power of the output signal of the first MTI filter (WF1*b*) 18B for the Q signal Q3. Furthermore, the velocity/power estimation circuit 21 estimates the velocity signal V and the variance signal T using the self correlation method. Then, the velocity/power estimation circuit 21 outputs the power signal P, the velocity signal V, and the variance signal T to the image display system 7 as the color Doppler data.

The image display system 7 performs necessary processing such as processing for generating a composite image based on the B-mode data and the color Doppler data, coordinate transformation, etc. The image data thus generated in the final stage is transmitted to the monitor 8, thereby displaying the image thus generated. Thus, the monitor 8 displays the B-mode image and the color Doppler image in a superimposed manner.

Next, description will be made regarding the effects provided by setting the properties of the first MTI filters (WF1*a*, WF1*b*) 18A and 18B, the second MTI filter (WF2) 19, and the third MTI filter (WF3) 20 as described above. Before this description, first, description will be made regarding what can cause motion artifacts to occur.

Japanese Unexamined Patent Application publication No. 2005-312773 discloses an arrangement which performs processing for suppressing motion artifacts utilizing an IQ signal and the amplitude signal of the IQ signal, which is equivalent to instantaneous clutter velocity correction. That is to say, with such an arrangement, the instantaneous clutter velocity is corrected by removing the low-frequency components from the IQ signal and the amplitude signal of the IQ signal. Here, description will be made regarding the physical significance of the instantaneous clutter phase correction.

As an assumption, let us say that the tissue moves at a constant velocity with a constant amplitude over a period of time (which will be referred to as the "packet time" hereafter) necessary for transmission/reception of the ultrasonic waves performed multiple times in order to acquire the Doppler signals. In this case, the amplitude signal of the clutter signal from the tissue is a DC signal.

Accordingly, such a signal can be removed by an MTI filter. On the other hand, the velocity and amplitude of the blood flow signal from the blood flow changes during the packet time. Accordingly, the amplitude signal of the blood flow signal is not removed by the MTI filter. Accordingly, the blood flow signals from the heart or from within large blood vessels is removed by performing the instantaneous phasing correction processing which removes low-frequency components from the IQ signal and the amplitude signal of the IQ signal. Accordingly, instantaneous phasing correction processing is performed only for the signals from tissues that move at a low velocity.

However, in actuality, the instantaneous phasing correction processing is not sufficient to remove motion artifacts. Accordingly, it can be understood that the assumption that the tissue moves at a constant velocity with a constant amplitude during the packet time is incorrect. However, the actual phenomenon does not agree with the assumption that the echo occurs due to reflection from the tissue.

The distance of the movement of the tissue in the abdominal region must not exceed around 6 mm/s. Here, the normalized Doppler frequency (Doppler frequency normalized with a Nyquist frequency of 0.5) fdnormal is represented by a following equation (2) with the mean frequency as f0, the pulse repetition frequency as PRF, the speed of sound as C, and the reflector migration velocity as v.

$$fd\text{normal}=2vf0/(C*PRF)=2v(PRF*k) \quad (2)$$

Here, in the equation (2), k represents the wavelength. Let us say that the migration velocity v of the reflector tissue is 6 mm/s, the mean frequency f0 is 2.5 MHz, the pulse repetition frequency PRF is 1 kHz, and the speed of sound C is 1540 m/s. In this case, the normalized Doppler frequency fdnorm is calculated to be 0.02 according to the equation (2). Accordingly, the tissue movement causes a 2% phase shift of the wavelength λ. Let us say that the number of repeated transmissions of ultrasonic waves N is 10. In this case, a 0.2% phase shift occurs. Ordinarily, the wave train length of the ultrasonic pulse is 2 to 4 for acquiring the color Doppler data. Accordingly, it can be assumed that the change in the envelope of the ultrasonic pulses is almost zero. Accordingly, it is concluded that the phase and the amplitude of the Doppler signal at the same position are constant during the packet time on the assumption that the echo occurs due to reflection from the tissue.

Figure 4:
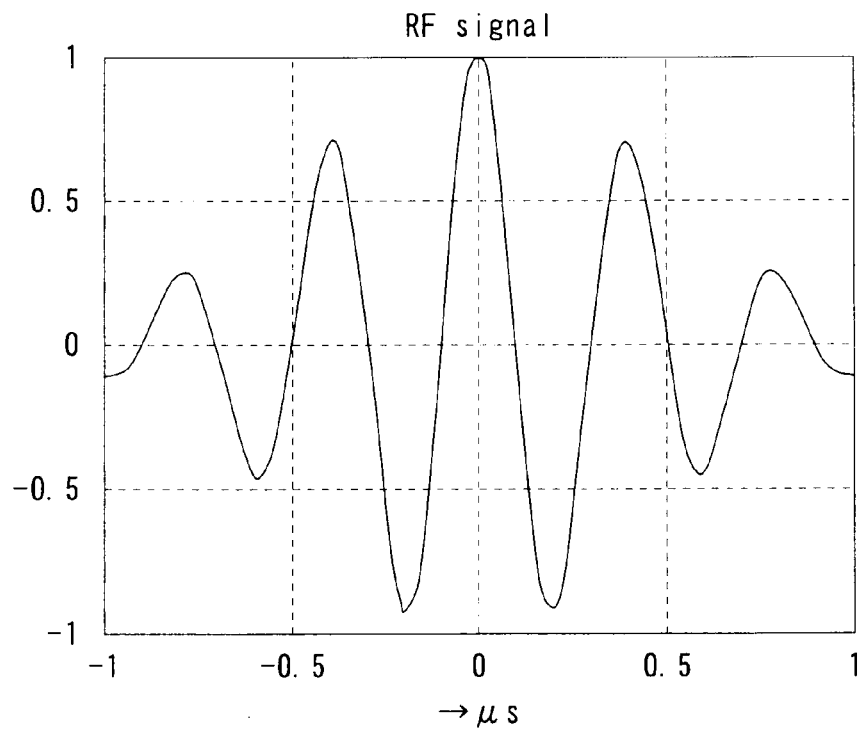
FIG. 4 is a diagram which shows an example of a received high frequency (RF: radio frequency) signal acquired after one transmission of ultrasonic waves to a point-shaped reflector.
Figure 5:
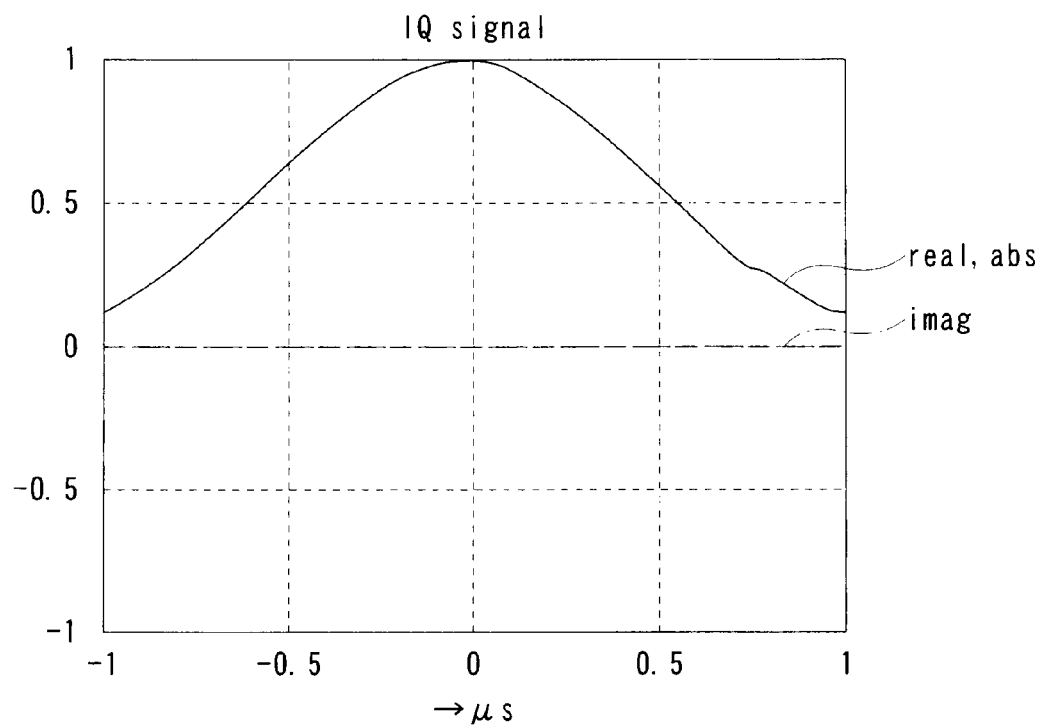
FIG. 5 is a diagram which shows the IQ signal generated based on the received RF signal from a point-shaped reflector shown in FIG. 4.
Figure 6:
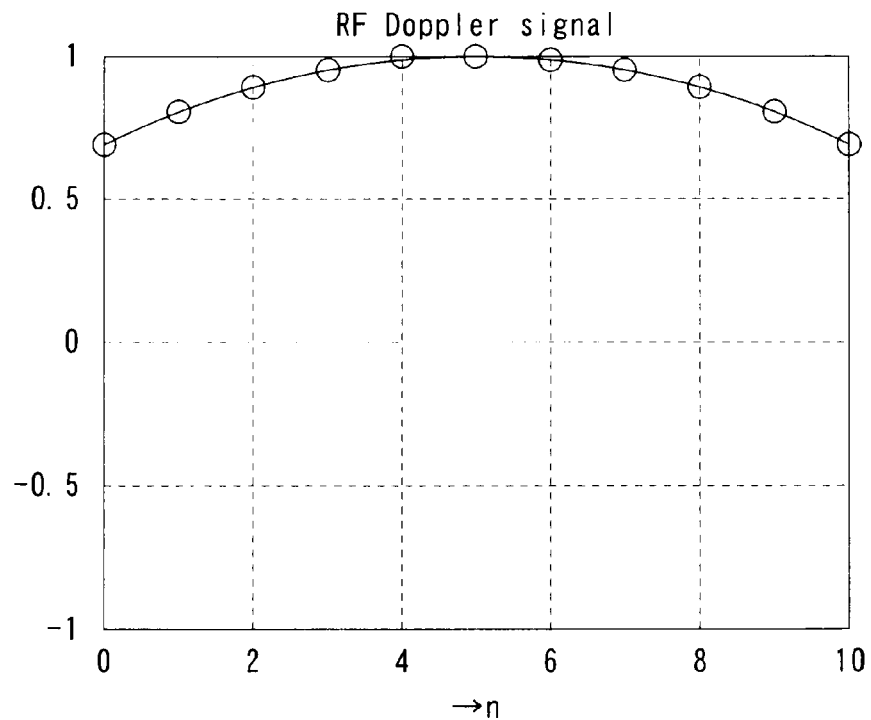
FIG. 6 is a diagram which shows an RF Doppler signal received from the point-shaped reflector with a normalized Doppler frequency of 0.02 at the point in time t=0 μs, which is obtained based on the received RF signal shown in FIG. 4.
Figure 7:
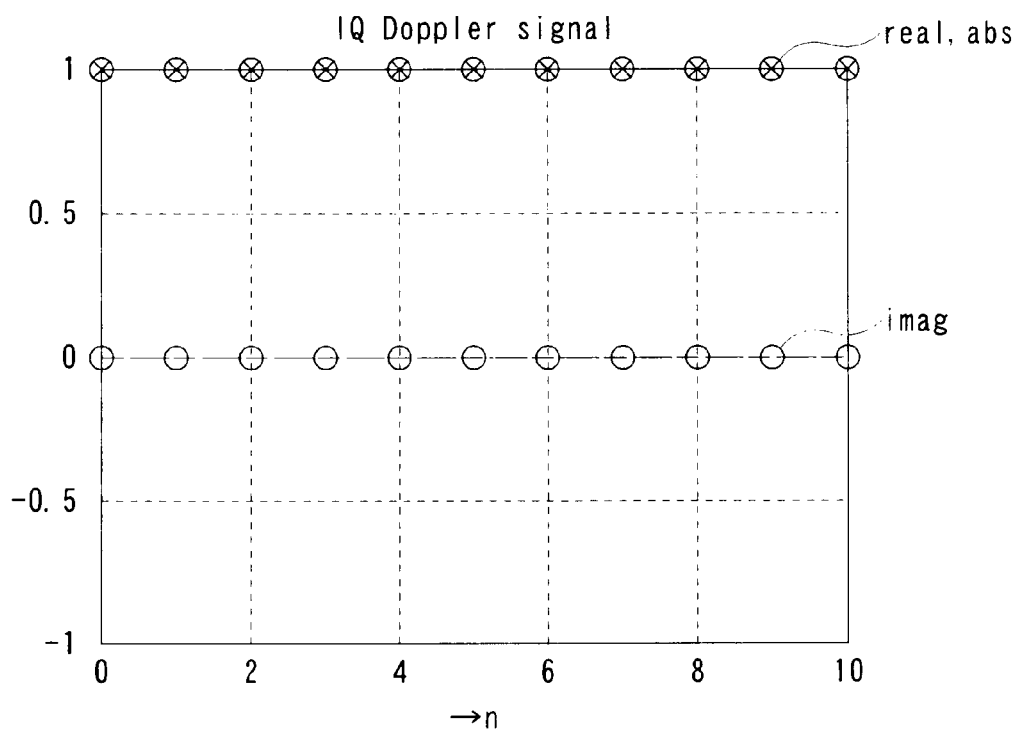
FIG. 7 is a diagram which shows an IQ Doppler signal from the point-shaped reflector, which is obtained based on the IQ signal shown in FIG. 5.

FIG. 4 is a diagram which shows an example of a received high frequency (RF: radio frequency) signal acquired after one transmission of ultrasonic waves to a point-shaped reflector. FIG. 5 is a diagram which shows the IQ signal generated based on the received RF signal from the point-shaped reflector shown in FIG. 4. FIG. 6 is a diagram which shows an RF Doppler signal received from the point-shaped reflector with a normalized Doppler frequency of 0.02 at the point in time t=0 μs, which is obtained based on the received RF signal shown in FIG. 4. FIG. 7 is a diagram which shows the IQ Doppler signal from the point-shaped reflector, which is obtained based on the IQ signal shown in FIG. 5.

As shown in FIG. 7, the change in the amplitude of the IQ Doppler signal is almost zero. However, in actuality, the echo received from the tissue is not due to the reflection of the ultrasonic waves, but is due to scattering thereof. The image generated based on the echo thus generated due to such scattering from the tissue has a speckle pattern, leading to a granular image. The speckle pattern occurs due to phase interference. The phase of this signal changes in a non-linear manner along the distance direction. Furthermore, the amplitude thereof repeatedly increases and decreases along the distance direction. The speckle pattern changes even due to slight movement of the tissue. Accordingly, the phase and the amplitude of the echo change due to such slight movement of the tissue. Accordingly, when the echo occurring due to the scattering from the tissue at the same position is observed in the form of a Doppler signal, the phase and the amplitude of the echo change with a shorter cycle than that of the actual movement of the tissue.

Figure 8:
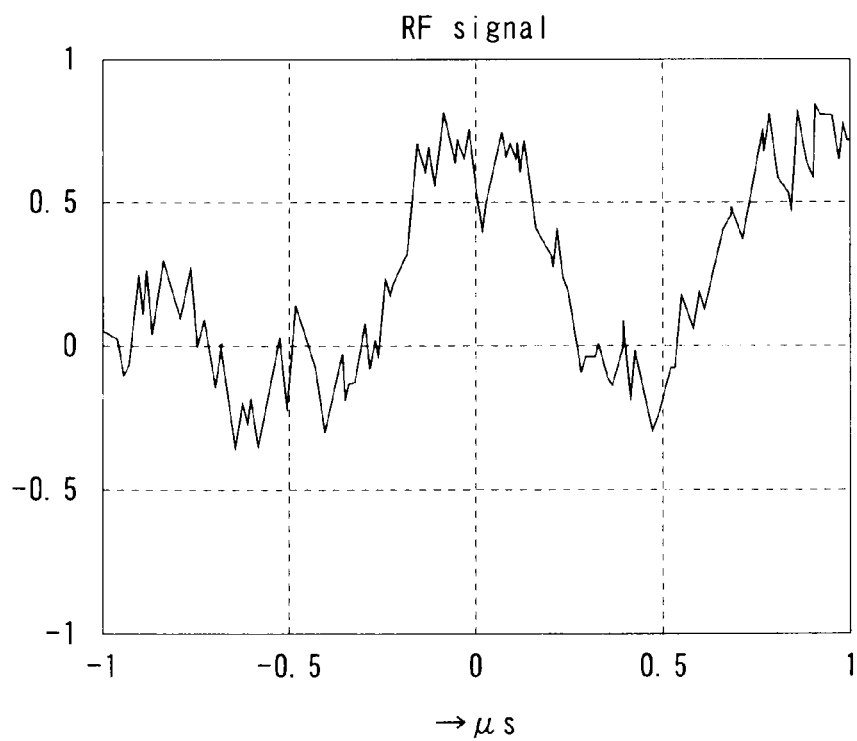
FIG. 8 is a diagram which shows an example of the received RF signal acquired after one transmission of ultrasonic waves to a scattering object.
Figure 9:
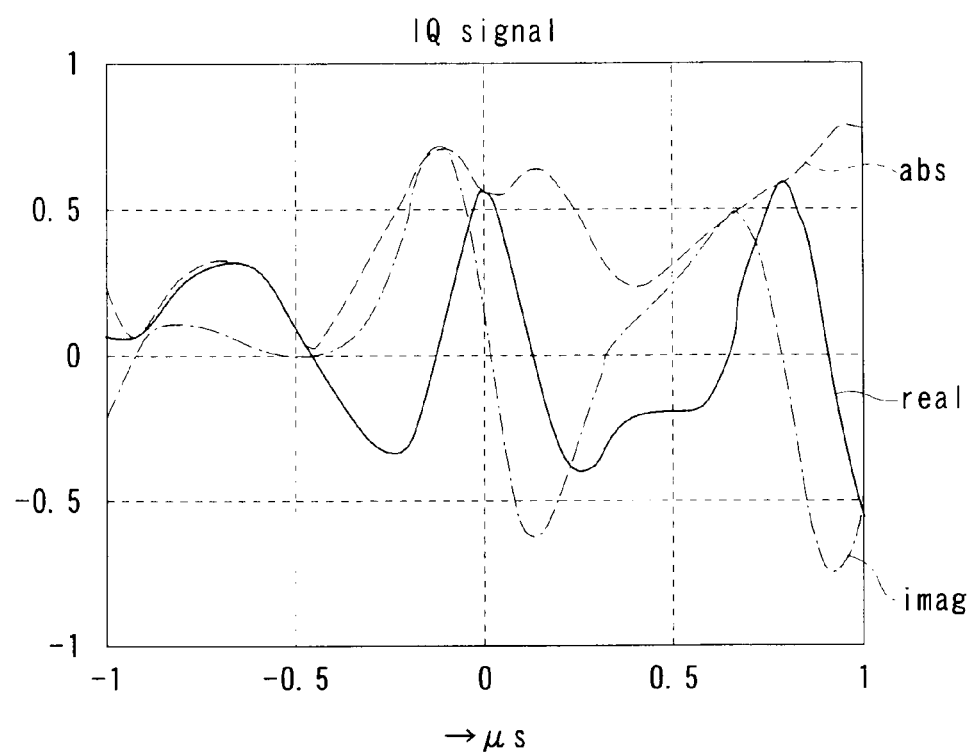
FIG. 9 is a diagram which shows the IQ signal generated based on the received RF signal from the scattering object.
Figure 10:
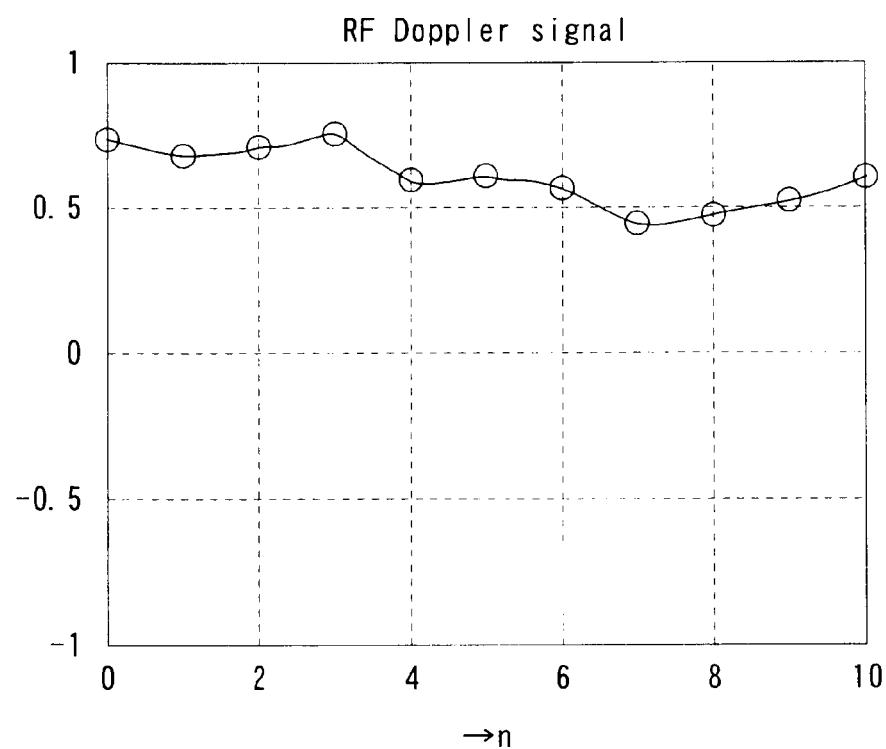
FIG. 10 is a diagram which shows the RF Doppler signal received from the scattering object, with the normalized Doppler frequency of 0.02 at the point in time t=0 μs, which is obtained based on the received RF signal shown in FIG. 8.
Figure 11:
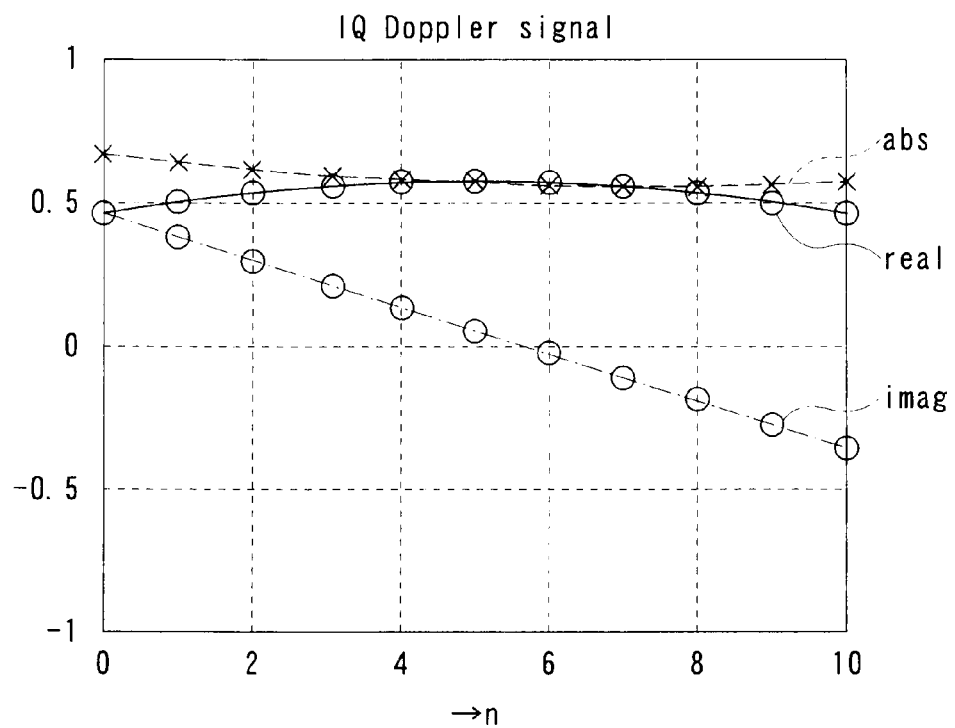
FIG. 11 is a diagram which shows the IQ Doppler signal from the scattering object, which is obtained based on the IQ signal shown in FIG. 9.

FIG. 8 is a diagram which shows an example of a received RF signal acquired after one transmission of ultrasonic waves to a scattering object. FIG. 9 is a diagram which shows the IQ signal generated based on the received RF signal from the scattering object. FIG. 10 is a diagram which shows an RF Doppler signal received from the scattering object, with a normalized Doppler frequency of 0.02 at the point in time t=0

μs, which is obtained based on the received RF signal shown in FIG. 8. FIG. 11 is a diagram which shows the IQ Doppler signal from the scattering object, which is obtained based on the IQ signal shown in FIG. 9.

As shown in FIG. 11, it can be understood that the value of each of the I (real) signal, the Q (imag) signal, and the amplitude (abs) signal changes. In a case in which only the phase of the clutter signal changes, the clutter signal can be suppressed by performing instantaneous phase correction or by acquiring the amplitude signal. However, in a case in which there is a change in the amplitude of the clutter signal, performing instantaneous phase correction or acquiring the amplitude signal is not sufficient to suppress the clutter signal. The reason is that the change in the amplitude of the clutter signal causes signal components that pass through the MTI filter. This is the actual source of motion artifacts.

On the other hand, a spatial compound method and a frequency compound method are known as a conventional technique for removing the speckle pattern occurring in a B-mode image. As described above, the speckle pattern occurs due to the phase interference, and due to the coherent ultrasonic wave. In order to solve this problem, with the spatial compound method, the amplitude signals of two kinds of received signals are acquired via the two partitions of the reception opening of the probe 2, and these two kinds of signals are added, which is incoherent processing, thereby reducing the speckle pattern. On the other hand, with the frequency compound method, a single received signal received from the probe 2 is divided into two bands of received signals, the amplitude signals are acquired for the respective these two bands of received signals, and the amplitude signals thus acquired are added.

Figure 12:
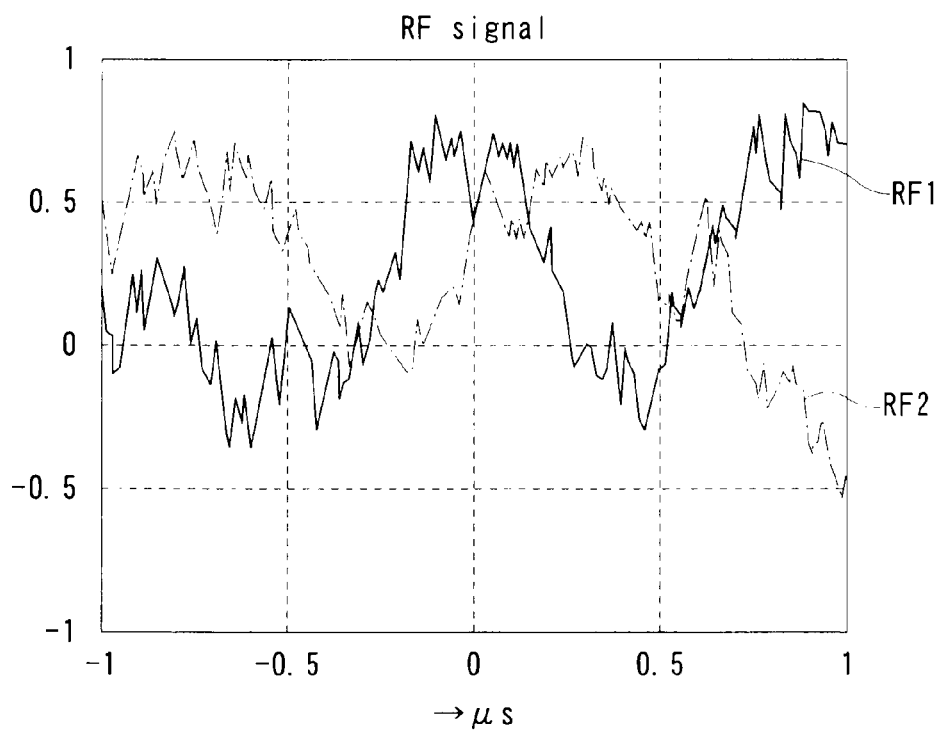
FIG. 12 is a diagram which shows the received RF signals RF1 and RF2, which are two kinds of received RF signals independent of one another, each of which is acquired after one transmission of ultrasonic waves.
Figure 13:
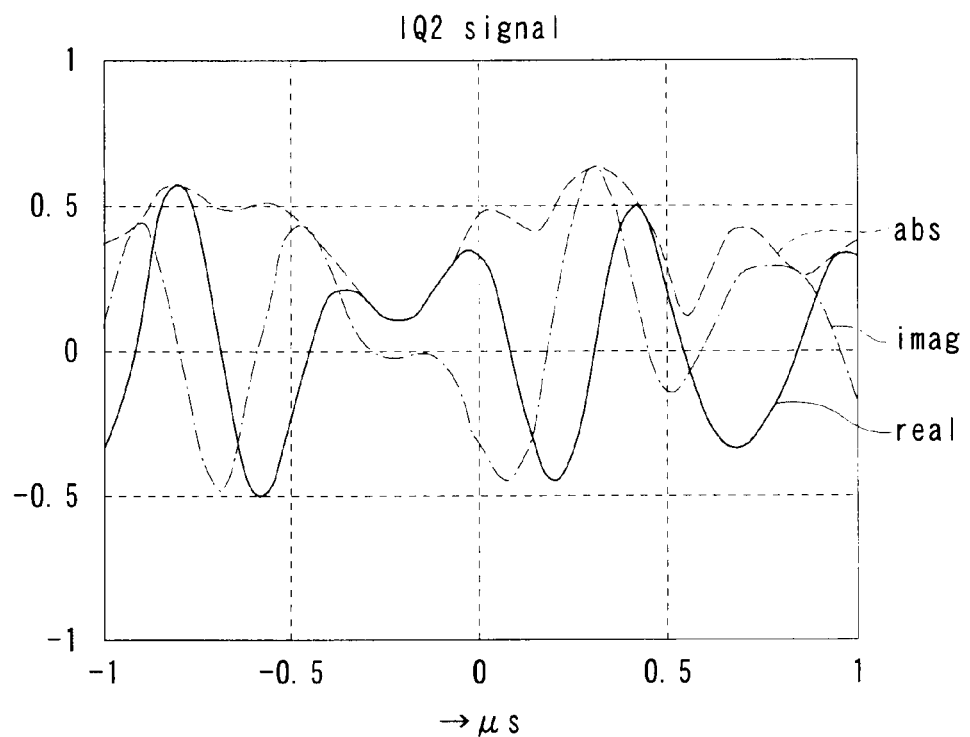
FIG. 13 is a diagram which shows the IQ signal generated based on the received RF signal RF2 which is one of the received RF signals shown in FIG. 12.
Figure 14:
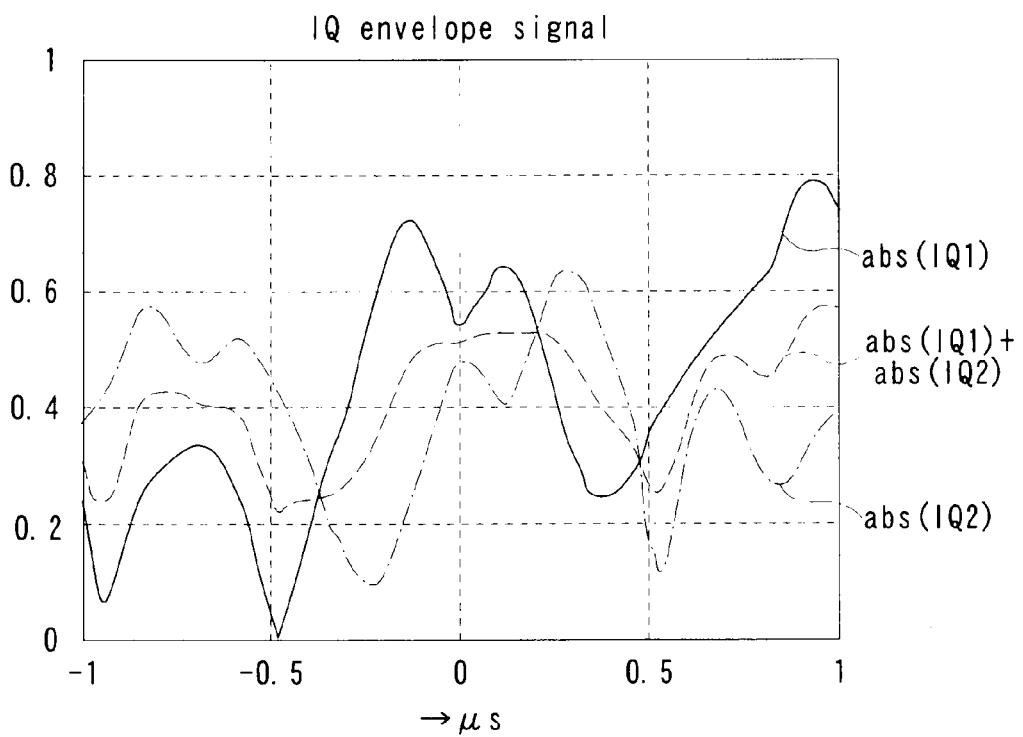
FIG. 14 is a diagram which shows amplitude signals abs (IQ1) and abs(IQ2) of the IQ signals IQ1 and IQ2 generated based on the two kinds of received RF signals RF1 and RF2 shown in FIG. 12, and the added signal abs(IQ1)+abs(IQ2) obtained by adding the amplitude signals abs(IQ1) and abs (IQ2)
Figure 15:
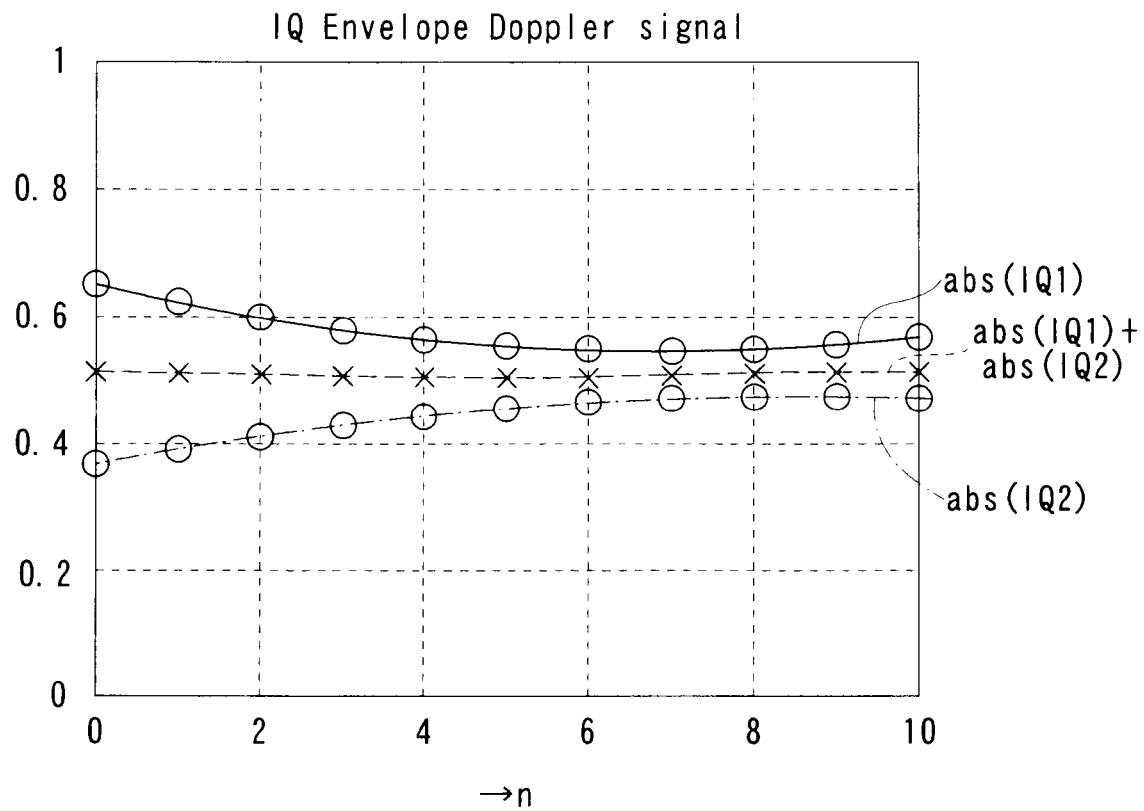
FIG. 15 is a diagram which shows a Doppler signal generated based on the two kinds of received RF signals RF1 and RF2 shown in FIG. 12 with the compound processing shown in FIG. 14.

FIG. 12 is a diagram which shows the received RF signals RF1 and RF2, which are two kinds of received RF signals independent of one another, each of which is acquired after one transmission of ultrasonic waves. FIG. 13 is a diagram which shows the IQ signal generated based on the received RF signal RF2 which is one of the received RF signals shown in FIG. 12. FIG. 14 is a diagram which shows amplitude signals abs(IQ1) and abs(IQ2) of the IQ signals IQ1 and IQ2 generated based on the two kinds of received RF signals RF1 and RF2 shown in FIG. 12, and the added signal abs(IQ1)+abs(IQ2) obtained by adding the amplitude signals abs(IQ1) and abs (IQ2). FIG. 15 is a diagram which shows a Doppler signal generated based on the two kinds of received RF signals RF1 and RF2 shown in FIG. 12 with the compound processing shown in FIG. 14.

It should be noted that the received RF signal RF1 which is one of the received RF signals shown in FIG. 12 is the same as the received RF signal RF shown in FIG. 8. Accordingly, the IQ signal generated based on the received RF signal RF1 is also the same as the IQ signal shown in FIG. 8.

It can be understood from FIG. 15 that the clutter signal is suppressed by the compound processing, and accordingly, the Doppler signal generated based on the added signal abs (IQ1)+abs(IQ2) is an approximately constant value.

With conventional techniques, such incoherent compound processing including addition is performed for B-mode data. However, such incoherent compound processing has not been performed for color Doppler data, because, with conventional techniques, the phase difference of the received signal is detected so as to estimate the velocity, thereby obtaining the color Doppler data. Accordingly, conventional techniques have been made on the assumption that such incoherent processing cannot be performed for the color Doppler data. In other words, in conventional techniques, it has been assumed that an IQ signal is required for acquisition of a blood flow signal.

On the other hand, as described above, Japanese Unexamined Patent Application publication No. 2005-312773 suggests that the blood flow signal can be obtained utilizing the amplitude signal. Accordingly, although it has been believed in conventional techniques that such compound processing cannot be performed for the color Doppler data, it can be expected that the compound processing can be performed for the color Doppler data on the assumption that the blood flow signal can also be obtained utilizing the amplitude signal.

Accordingly, as shown in FIG. 3, the first amplitude acquisition circuit 11, the second amplitude acquisition circuit 12, and the third adder 16 as a common adder, are included. With such an arrangement, the reception opening of the probe 2 is partitioned into two regions, and the spatial compound processing is performed, thereby reducing the speckle pattern occurring in the color Doppler data. Accordingly, the added signal A12 input from the third adder 16 to the third MTI filter (WF3) 20 corresponds to the amplitude signal subjected to the spatial compound processing.

Furthermore, the properties of the first MTI filters (WF1*a*, WF1*b*) 18A and 18B, the second MTI filter (WF2) 19, and the third MTI filter (WF3) 20 are set so as to perform the spatial compound processing only for predetermined frequencies of IQ signals. The equations (1-1), (1-2), and (1-3) represent an example of the properties of the first MTI filters (WF1*a*, WF1*b*) 18A and 18B, the second MTI filter (WF2) 19, and the third MTI filter (WF3) 20 thus set.

It should be noted that Unexamined Patent Application publication No. 2005-312773 describes in detail the setting method for setting the properties of the first MTI filters (WF1*a*, WF1*b*) 18A and 18B, the second MTI filter (WF2) 19, and the third MTI filter (WF3) 20 so as to perform the spatial compound processing only for predetermined frequencies of IQ signals. Let us say that the properties of the first MTI filters (WF1*a*, WF1*b*) 18A and 18B, the second MTI filter (WF2) 19, and the third MTI filter (WF3) 20 are set to those represented by the equations (1-1), (1-2), and (1-3). In this case, the signal filtering is performed as follows. That is to say, of the ordinary IQ signal IQ3 obtained by adding the two kinds of IQ signals IQ1 and IQ2, the first MTI filters (WF1*a*, WF1*b*) 18A and 18B allow the high-range frequency components equal to or higher than the frequency f3 to pass through the filter as they are. Of the amplitude signal A3 of the ordinary IQ signal IQ3 obtained by adding the two kinds of IQ signals IQ1 and IQ2, the second MTI filter (WF2) 19 allows the middle-range frequency components ranging from the frequency f2 to the frequency f3 to pass through the filter. Of the added signal A12 that corresponds to the amplitude signal subjected to the spatial compound processing, the third MTI filter (WF3) 20 allows the low-range frequency components ranging from the frequency f1 to the frequency f2 to pass through the filter.

In other words, in the color Doppler processing system 6, for the high-range frequency components of the input IQ signal IQ, the first MTI filters (WF1*a*, WF1*b*) 18A and 18B allow the ordinary IQ signal IQ3 to pass through the filter. For the middle-range frequency components thereof, the second MTI filter (WF2) 19 allows the amplitude signal A3 of the IQ signal IQ3 to pass through the filter. For the low-range frequency components thereof, the third MTI filter (WF3) 20 allows the added signal A12 subjected to the spatial compound processing to pass through the filter. On the other hand, the lowest-range frequency components of the IQ signal IQ which are equal to or lower than the frequency f1 are cut off by each of the first MTI filters (WF1a, WF1b) 18A and 18B, the second MTI filter (WF2) 19, and the third MTI filter (WF3) 20.

Such filtering processing allows the motion artifacts due to the change in the amplitude of the speckle pattern to be removed without removing the blood flow signals. That is to say, the blood flow moving at a high velocity is a scattering object which moves at a high speed with a certain distribution. Accordingly, with respect to the resulting high velocity blood flow signals, the compound processing cannot suppress the change in the amplitude. That is to say, the compound processing has only a small effect on such a blood flow signal. Accordingly, for a blood flow signal that results from high velocity blood flow, the IQ signal IQ3 is employed, thereby providing a blood flow signal which has not been reduced.

Conversely, for the IQ signal that results from the blood or tissue moving at a low velocity, the spatial compound processing is used, thereby reducing the speckle pattern. Thus, such an arrangement provides the added signal A12 that has been subjected to the spatial compound processing, thereby reducing the adverse effects of the motion artifacts.

On the other hand, for the IQ signal that results from the blood or tissue moving at a middle-range velocity, the amplitude signal A3 without phase information is used. This processing is not as effective in reducing the speckle pattern as compared with the spatial compound processing. However, such processing is capable of reducing the adverse effects of the motion artifacts without removing the blood flow signal that results from the blood flow moving at a low velocity.

As described above, such an arrangement suppresses the change in the amplitude of the IQ signal, thereby returning the clutter signal frequencies, which occur because the tissue is moving at a low velocity and which extend into the high-frequency range because of the change in the amplitude due to the speckle pattern, to the low-frequency range that corresponds to the actual movement velocity of the tissue. Thus, such an arrangement allows the clutter signals to be effectively removed using the MTI filters.

Most of the clutter signals and the amplitude signals of the clutter signals range from the DC level to the low-frequency range. Thus, such an arrangement is capable of detecting the blood flow signal at a low-frequency range while suppressing occurrence of motion artifacts. That is to say, such an arrangement is capable of detecting the blood flow moving at a low velocity while suppressing the adverse effects of the clutter signals.

Also, the color Doppler processing system 6 may have a configuration without a function for generating the amplitude signal A3 of the IQ signal IQ3 and a function of the second MTI filter (WF2) 19 for performing the filtering processing. While such an arrangement has only the function of the spatial compound processing, such an arrangement also provides the advantage of reducing the motion artifact.

Description has been made with reference to FIG. 3 regarding the configuration of the color Doppler processing system 6, which has a partitioned reception opening so as to perform the spatial compound processing for the color Doppler data. Also, as described above, frequency compound processing, small-angle compound processing, or the like may be performed for the color Doppler data. Also, an arrangement may be made having a partitioned transmission opening so as to perform the spatial compound processing. In addition, a combination of such multiple kinds of compound processing may be performed for the color Doppler data.

In the small-angle compound processing, the deflection angle is changed in a small range, which is equal to or smaller than the resolution, so as to acquire two kinds of IQ signals IQ1 and IQ2, and the amplitude signals A1 and A2 of the IQ1 and IQ2 are added. In the small-angle compound processing, these two kinds of IQ signals IQ1 and IQ2 are acquired under respective interference conditions that spatially differ from one another, and thus the small-angle compound processing can be seen as a kind of spatial compound processing. Also, adjacent raster data may be used as the aforementioned two kinds of IQ signals IQ1 and IQ2. Such an arrangement also provides spatial compound processing with a resolution tradeoff.

On the other hand, frequency compound processing is a kind of compound processing in which the difference in the received frequency is employed as the interference condition.

Figure 16:
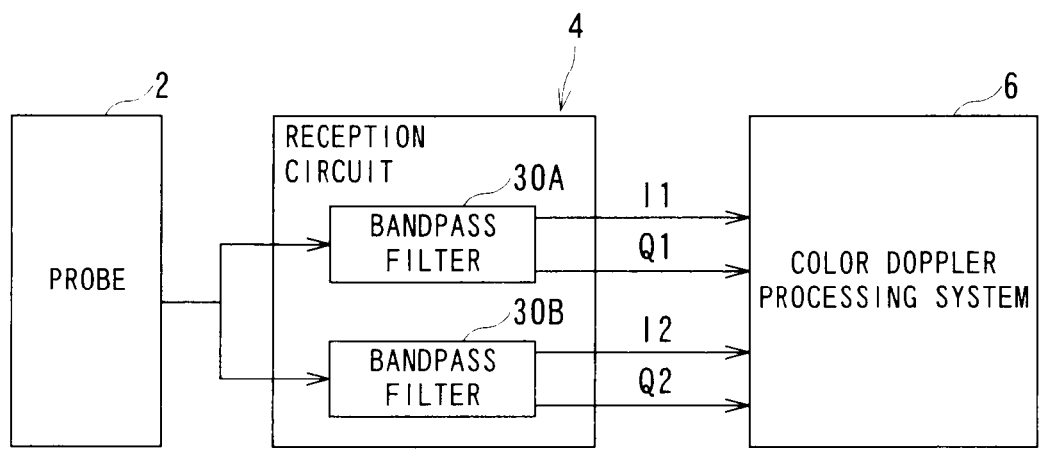
FIG. 16 is a diagram which shows a configuration of the ultrasonic diagnostic apparatus including the color Doppler processing system shown in FIG. 1, having a function of performing the frequency compound processing.

FIG. 16 is a diagram which shows a configuration of the ultrasonic diagnostic apparatus 1 including the color Doppler processing system 6 shown in FIG. 1, having a function of performing the frequency compound processing.

With such an arrangement in which the frequency compound processing is performed in the color Doppler processing system 6, two bandpass filters 30A and 30B are provided to the reception circuit 4 as shown in FIG. 16. The mean frequencies set for the bandpass filters 30A and 30B which allow the respective signals to pass through the filters are set to be different from one another. With such an arrangement, the received RF signal transmitted from the probe 2 to the reception circuit 4 is input to these bandpass filters 30A and 30B. Furthermore, these two bandpass filters 30A and 30B output two kinds of IQ signals IQ1 and IQ2 which are transmitted to the color Doppler processing system 6. The color Doppler processing system 6 adds the amplitude signals A1 and A2 of these two IQ signals IQ1 and IQ2, thereby performing frequency compound processing.

That is to say, the ultrasonic diagnostic apparatus 1 having such a configuration acquires two kinds of IQ signals under respective interference conditions that differ from one another in a spatial or frequency manner. These two kinds of IQ signals are added, and the amplitudes of these two kinds of IQ signals are added. Then, MTI filters having respective properties that differ from one another are applied to the added IQ signal and the added amplitude signal thus generated, thereby generating a Doppler signal while reducing motion artifacts that result from the change in the amplitude of the tissue speckle pattern. Furthermore, as necessary, the ultrasonic diagnostic apparatus 1 applies an MTI filter having a different property to the amplitude signal of the added IQ signal obtained by adding these two kinds of IQ signals, thereby extracting the Doppler signal that correspond to a predetermined movement velocity while reducing the motion artifacts.

In other words, with such an arrangement, the compound processing is performed for the color Doppler data that results from the blood flow or tissue moving in a predetermined velocity range. Furthermore, the amplitude signal thereof is employed as the Doppler signal as necessary.

With such an arrangement, the ultrasonic diagnostic apparatus 1 has a relatively simple circuit configuration which provides a function of performing the compound processing, thereby reducing the change in the amplitude of the speckle pattern. Thus, such an arrangement is capable of reducing motion artifacts, which are difficult to remove using another arrangement that uses the amplitude signal. With such an arrangement, the signal components subjected to the compound processing are used as the Doppler signal in a low frequency range. Generally, such an arrangement is capable of acquiring the blood flow signals in a low-frequency range while reducing the motion artifacts.

Figure 17:
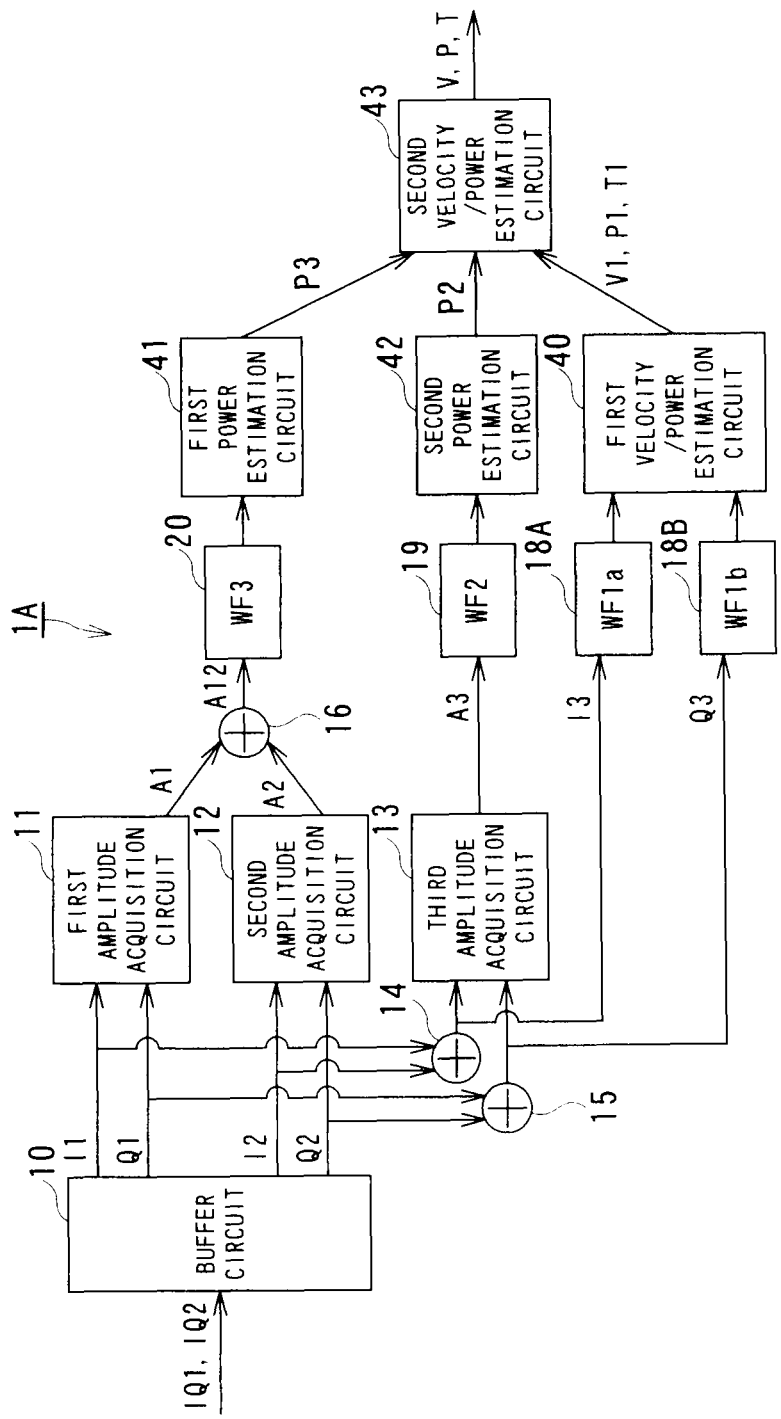
FIG. 17 is a block configuration diagram which shows an ultrasonic diagnostic apparatus according to a second embodiment of the present invention.

FIG. 17 is a block configuration diagram which shows an ultrasonic diagnostic apparatus according to a second embodiment of the present invention.

In an ultrasonic diagnostic apparatus 1A shown in FIG. 17, the circuit configurations on the output sides of the first MTI filters (WF1a, WF1b) 18A and 18B, the second MTI filter (WF2) 19, and the third MTI filter (WF3) 20 differ from those of the ultrasonic diagnostic apparatus 1 shown in FIG. 1. The other configurations and operations are substantially the same as those of the ultrasonic diagnostic apparatus 1 shown in FIG. 1. Accordingly, only the circuit configuration of the color Doppler processing system 6A is shown. The components in common for both figures are denoted by the same reference numerals, and description thereof will be omitted.

That is to say, in the color Doppler processing system 6A of the ultrasonic diagnostic apparatus 1A, a first velocity/power estimation circuit 40 is connected to the output sides of the first MTI filters (WF1a, WF1b) 18A and 18B as a common component. Furthermore, a first power estimation circuit 41 and a second power estimation circuit 42 are connected to the output sides of the third MTI filter (MF3) 20 and the second MTI filter (WF2) 19, respectively. Furthermore, each of the output sides of the first velocity/power estimation circuit 40, the first power estimation circuit 41, and the second power estimation circuit 42 is connected to the second velocity/power estimation circuit 43 which is a common component. The output side of the second velocity/power estimation circuit 43 is connected to the image display system 7 which is a downstream system.

The first velocity/power estimation circuit 40 estimates the velocity signal V1, the variance signal T1, and the power signal P1 based on the output signals of the first MTI filters (WF1a, WF1b) 18A and 18B. The first power estimation circuit 41 estimates the power signal P2 based on the output signal of the second MTI filter (WF2) 19. The second power estimation circuit 42 estimates the power signal P3 based on the output signal of the third MTI filter (WF3) 20.

Then, the second velocity/power estimation circuit 43 estimates the velocity signal V, the variance signal T, and the power signal P, each of which is used in the output signal of the color Doppler system 6A in the final stage, based on the velocity signal V1, the variance signal T1, and the power signal P1 estimated by the first velocity/power estimation circuit 40, the power signal P2 estimated by the first power estimation circuit 41, and the power signal P3 estimated by the power estimation circuit 42.

The velocity signal V, the variance signal T, and the power signal P are estimated by the second velocity/power estimation circuit 43 as follows. That is to say, the velocity signal V1 and the variance signal T1 estimated by the first velocity/power estimation circuit 40 are used as the velocity signal V and the variance signal T in the final stage. Furthermore, in a case in which the difference between the three power signals P1, P2, and P3 is not large, i.e., in a case in which the difference between the power signals P1, P2, and P3 is equal to or smaller than a predetermined value, the power signal P1 estimated by the first velocity/power estimation circuit 40 is used as the power signal P in the final stage. On the other hand, in a case in which the power signal (P1, P2, and P3) increases according to an increase in the frequency components thereof, i.e., in a case of P1>P2>P3, the power signal P is calculated by performing weighting addition of the three power signals P1, P2, and P3 as represented by a following equation (3), and the power signal P thus obtained is output.

$$P = aP1 + bP2 + cP3 \qquad (3)$$

Here, each of a, b, and c represents a weighting coefficient, and satisfies the condition a<b<c.

As described above, the second velocity/power estimation circuit 43 outputs the velocity signal V, the variance signal T, and the power signal P which is obtained by performing the weighting addition of the power signals P1, P2, and P3 as necessary based on the relation among the three power signals P1, P2, and P3. These weighting coefficients are set to those which effectively reduce the motion artifacts in the color Doppler image.

The image display system 7 is capable of displaying the color Doppler image in various display formats. In general, examples of the display formats for a color Doppler image include: a display format in which only the power signal P is displayed; a display format in which only the velocity signal V is displayed; and a display format in which the velocity signal V and the variance signal T are displayed. In a case of a display format for a color Doppler image in which only the power signal P is displayed, the power signal P may be displayed as it is. Alternatively, in this case, an arrangement may be made in which a lower threshold is set for the power signal P, and threshold processing is performed so as to cut off the noise-level signals, following which the power signal P is displayed. On the other hand, in a case of a display format for a color Doppler image in which only the velocity signal V is displayed, or in a case of a display format in which the velocity signal V and the variance signal T are displayed, the lower thresholds are set for the power signal P and the velocity signal V. With such an arrangement, in a case in which either the power signal P or the velocity signal V is equal to or smaller than the corresponding lower threshold, the color display is not performed.

With such an arrangement, weighting addition of the power signals P1, P2, and P3 is performed using the weighting coefficients a, b, and c which are determined based on the values of the three power signals P1, P2, and P3 so as to effectively remove motion artifacts from a color Doppler image.

As described above, the ultrasonic diagnostic apparatus 1A is capable of performing complex signal processing by adjusting the weighting coefficients a, b, and c which are variable parameters, in addition to the advantages of the ultrasonic diagnostic apparatus 1 shown in FIG. 1.

Figure 18:
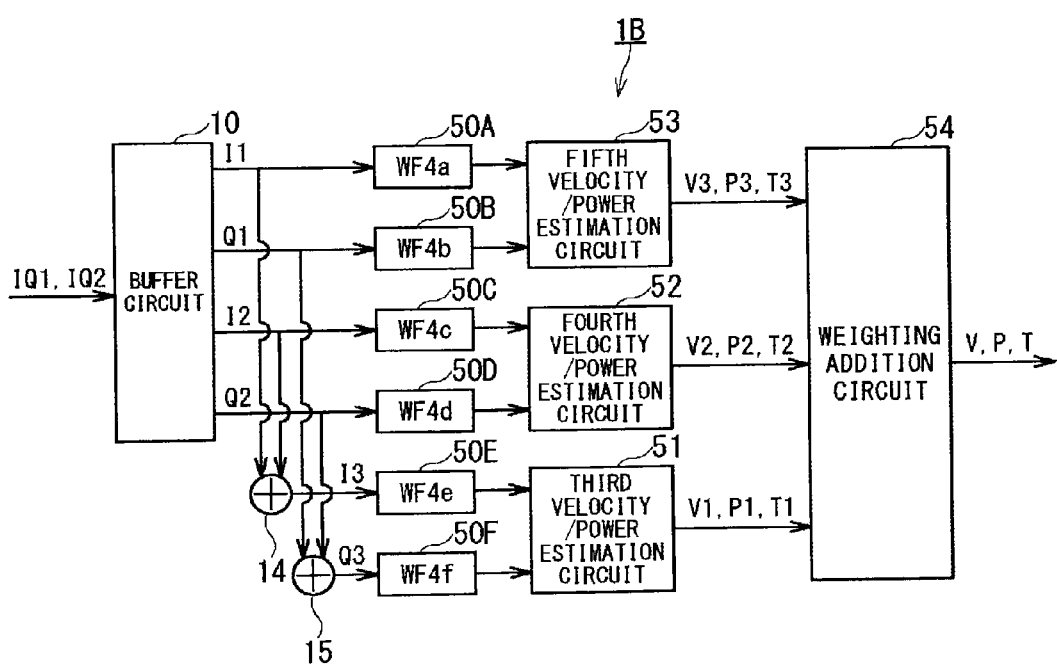
FIG. 18 is a block configuration diagram which shows an ultrasonic diagnostic apparatus according to a third embodiment of the present invention.

FIG. 18 is a block configuration diagram which shows an ultrasonic diagnostic apparatus according to a third embodiment of the present invention.

In an ultrasonic diagnostic apparatus 1B shown in FIG. 18, the circuit configuration of a color Doppler processing system 6B differs from that included in the ultrasonic diagnostic apparatus 1 shown in FIG. 1. The other configurations and operations are substantially the same as those of the ultrasonic diagnostic apparatus 1 shown in FIG. 1. Accordingly, only the circuit configuration of the color Doppler processing system 6B is shown. The components in common for both figures are denoted by the same reference numerals, and description thereof will be omitted.

The color Doppler processing system 6B of the ultrasonic diagnostic apparatus 1B includes six fourth MTI filters (WF4a, WF4b, WF4c, WF4d, WF4e, WF4f) 50A, 50B, 50C, 50D, 50E, and 50F, a third velocity/power estimation circuit 51, a fourth velocity/power estimation circuit 52, a fifth velocity/power estimation circuit 53, and a weighting addition circuit 54, in addition to the buffer circuit 10, the first adder 14, and the second adder 15. The first adder 14, the second adder 15, and the four fourth MTI filters (WF4a, WF4b, WF4c, WF4d) 50A, 50B, 50C, and 50D are connected to the output side of the buffer circuit 10.

It should be noted that the I signal I1 that corresponds to the first channel through the N/2'th channel is input to the fourth MTI filter (WF4a) 50A from the opening 1 via the buffer circuit 10. The Q signal Q1 that corresponds to the first channel through the N/2'th channel is input to the fourth MTI filter (WF4b) 50B from the opening 2 via the buffer circuit 10. The I signal I2 that corresponds to the (N/2+1)'th channel through the N'th channel is input to the fourth MTI filter (WF4c) 50C from the opening 1 via the buffer circuit 10. The Q signal Q2 that corresponds to the (N/2+1)'th channel through the N'th channel is input to the fourth MTI filter (WF4d) 50D from the opening 2 via the buffer circuit 10. Furthermore, the first adder 14 receives via the buffer circuit 10 the I signal I1 from the opening 1 that corresponds to the first channel through the N/2'th and the I signal I2 from the opening 2 that corresponds to the (N/2+1)'th channel through the N'th channel. Moreover, the second adder 15 receives via the buffer circuit 10 the Q signal Q1 that corresponds to the first channel through the N/2'th channel and the Q signal Q2 that corresponds to the (N/2+1)'th channel through the N'th channel.

The first adder 14 adds the I signals I1 and I2 output from the openings 1 and 2. Accordingly, the first adder 14 outputs the I signal I3 output from the entire opening. Similarly, the second adder 15 adds the Q signals Q1 and Q2 output from the openings 1 and 2. Accordingly, the second adder 15 outputs the Q signal Q3 output from the entire opening. Furthermore, the output sides of the first adder 14 and the second adder 15 are connected to the corresponding fourth MTI filters (WF4e, WF4f) 50E and 50F. Accordingly, these two fourth MTI filters (WF4e, WF4f) 50E and 50F receive the I signal I3 and the Q signal Q3 output from the entire opening, respectively.

That is to say, the fourth MTI filters (WF4a, WF4b) 50A and 50B correspond to the opening 1. The fourth MTI filters (WF4c, WF4d) 50C and 50D correspond to the opening 2. The fourth MTI filters (WF4e, WF4F) 50E and 50F correspond to the entire opening. Each of the fourth MTI filters (WF4a, WF4b, WF4c, WF4d, WF4e, WF4f) 50A, 50B, 50C, 50D, 50E, and 50F has properties similar to those of conventional MTI filters. That is to say, each of the fourth MTI filters (WF4a, WF4b, WF4c, WF4d, WF4e, WF4f) 50A, 50B, 50C, 50D, 50E, and 50F removes the frequency components of the input signal which are equal to or smaller than a predetermined value as clutter signals, thereby extracting the blood flow signals.

Furthermore, the output sides of the two fourth MTI filters (WF4a, WF4b) 50A and 50B that correspond to the opening 1 are connected to the fifth velocity/power estimation circuit 53 which is a common component. The output sides of the two fourth MTI filters (WF4c, WF4d) 50C and 50D that correspond to the opening 2 are connected to the fourth velocity/power estimation circuit 52 which is a common component. The output sides of the two fourth MTI filters (WF4e, WF4f) 50E and 50F that correspond to the entire opening are connected to the third velocity/power estimation circuit 51 which is a common component.

The third velocity/power estimation circuit 51 estimates the velocity signal V1, the variance signal T1, and the power signal P1 based on the blood flow signal thus input. The fourth velocity/power estimation circuit 52 estimates the velocity signal V2, the variance signal T2, and the power signal P2 based on the blood flow signal thus input. The fifth velocity/power estimation circuit 53 estimates the velocity signal V3, the variance signal T3, and the power signal P3 based on the blood flow signal thus input. These signals thus estimated are output to the weighting addition circuit 54.

That is to say, the color Doppler processing system 6B of the ultrasonic diagnostic apparatus 1B estimates the velocity signals V1, V2, and V3, the variance signals T1, T2, and T3, and the power signals P1, P2, and P3, based on the blood flow signals obtained by applying the fourth MTI filters (WF4a, WF4b, WF4c, WF4d, WF4e, WF4f) 50A, 50B, 50C, 50D, 50E, and 50F to the corresponding IQ signals IQ1, IQ2, and IQ3 output from the opening 1, the opening 2, and the entire opening.

The weighting addition circuit 54 performs weighting addition of the velocity signals V1, V2, and V3, the variance signals T1, T2, and T3, and the power signals P1, P2, and P3, that correspond to the opening 1, the opening 2, and the entire opening, as represented by a following equations (4-1), (4-2), and (4-3), thereby obtaining the velocity signal V, the variance signal T, and the power signal P to be displayed in the form of a color Doppler image in the final stage.

$$P = a1P1 + b1P2 + c1P3 \quad (4\text{-}1)$$

$$V = a2V1 + b2V2 + c2V3 \quad (4\text{-}2)$$

$$T = a3T1 + b3T2 + c3T3 \quad (4\text{-}3)$$

The weighting coefficients to be used for the weighting addition can be obtained in the same way as with the weighting coefficients a, b, and c used in the ultrasonic diagnostic apparatus 1A according to the second embodiment shown in FIG. 17. That is to say, the weighting coefficients a1, b1, c1, a2, b2, c2, a3, b3, and c3, are set to values which effectively reduce motion artifacts in a color Doppler image, based on the velocity signals V1, V2, and V3, the variance signals T1, T2, and T3, and the power signals P1, P2, and P3.

Description has been made regarding the ultrasonic diagnostic apparatus 1 according to the first embodiment with reference to FIG. 1, and the ultrasonic diagnostic apparatus 1A according to the second embodiment with reference to FIG. 2, each of which performs the compound processing by adding the amplitudes of the IQ signals before the input thereof to the MTI filters. Also, like the ultrasonic diagnostic apparatus 1B shown in FIG. 18, an arrangement may be made in which the velocity signals V1, V2, and V3, the variance signals T1, T2, and T3, and the power signals P1, P2, and P3 are estimated by simply applying conventional MTI filters to the corresponding IQ signals IQ1, IQ2, and IQ3 output from the opening 1, the opening 2, and the entire opening, and the averages or weighting additions of the velocity signals V1, V2, and V3, the variance signals T1, T2, and T3, and the power signals P1, P2, and P3 thus estimated are used as the velocity signal V, the variance signal T, and the power signal P which are used as the data to be displayed on the monitor 8. That is to say, each of the addition of the velocity signals V1, V2, and V3, the addition of the variance signals T1, T2, and T3, and the addition of the power signals P1, P2, and P3 is an incoherent calculation, thereby providing the advantage of reducing the speckle pattern.

With the ultrasonic diagnostic apparatus 1B having such functions, the weighting coefficients, each of which is a variable parameter, can be set for the velocity signals V1, V2, and V3, and the variance signals T1, T2, and T3, in addition to the power signals P1, P2, and P3. Thus, such an arrangement allows the user to perform fine control operations. For example, an arrangement may be made in which, in a case of P1>P2>P3, the weighting coefficients for the power signal P3, the velocity signal V3, and the variance signal T3 that correspond to the entire opening are increased.

As an example of a modification of the ultrasonic diagnostic apparatus 1B shown in FIG. 18, an arrangement may be made in which the power signals P1, P2, P3 and self-correlation functions are calculated for the opening 1, the opening 2, and the entire opening, instead of calculating the velocity signals V1, V2, and V3, and the variance signal T1, T2, and T3. Furthermore, the velocity signal V and the variance signal T are calculated in the final stage by performing weighting addition of the self-correlation functions using the weighting coefficients determined based on the power signals P1, P2, and P3. With such an arrangement, the power signal P is obtained by performing weighting addition of the power signals P1, P2, and P3.

What is claimed is:

1. An ultrasonic diagnostic apparatus, comprising:
processing circuitry configured to
acquire a plurality of ultrasonic reception IQ signals under respective interference conditions that differ from one another;
generate an added signal by adding up the ultrasonic reception IQ signals;
generate an added amplitude signal by adding up amplitudes of the ultrasonic reception IQ signals;
extract a first Doppler signal based on the added signal, that corresponds the first Doppler signal corresponding to motion; and
extract a second Doppler signal based on the added amplitude signal, the second Doppler signal having a property that differs from a property of the first Doppler signal,
wherein the processing circuitry is further configured to extract the first Doppler signal and the second Doppler signal, respectively, while reducing an artifact due to tissue motion.

2. The ultrasonic diagnostic apparatus according to claim 1, wherein the processing circuitry is further configured to
extract the second Doppler signal by using a filter having a property of passing only signal, acquired when a motion velocity of the tissue is not zero and is lower than a predetermined velocity, as a part of the added amplitude signal; and
extract the first Doppler signal by using a filter having a property of passing only signal, acquired when the motion velocity of the tissue is larger than the predetermined velocity, as a part of the added signal.

3. The ultrasonic diagnostic apparatus according to claim 1, wherein
the processing circuitry is further configured to perform a weighting addition of a power signal of the first Doppler signal and a power signal of the second Doppler signal, respectively, using weighting factors determined based on comparison results obtained by making a comparison between the power signal of the first Doppler signal and the power signal of the second Doppler signal.

4. The ultrasonic diagnostic apparatus according to claim 1, wherein
the processing circuitry is further configured to acquire the ultrasonic reception IQ signals by using at least one of a difference of a transmission opening, a difference of a reception opening, a difference of a scanning position changed by a scanning position changing, and a difference of a reception filter having a frequency property.

5. An ultrasonic diagnostic apparatus, comprising:
processing circuitry configured to
acquire a plurality of ultrasonic reception IQ signals under respective interference conditions that differ from one another;
detect a plurality of Doppler signals of the ultrasonic reception IQ signals based on the ultrasonic reception IQ signals, the plurality of Doppler signals including a first Doppler signal extracted based on an added signal generated by adding the ultrasonic reception IQ signals; and
calculate, for each of the plurality of Doppler signals, at least one of a self-correlation function, a blood flow velocity, a variance in the blood flow, and a blood flow power signal, and estimate at least one of an overall blood flow velocity, an overall blood flow variance, and an overall blood flow power signal by performing a weighted addition of the corresponding calculation results calculated for each of the plurality of Doppler signals.

6. The ultrasonic diagnostic apparatus according to claim 5, wherein processing circuitry is further configured to acquire the ultrasonic reception IQ signals by using at least one of a difference of a transmission opening, a difference of a reception opening, a difference of a scanning position changed by a scanning position changing, and a difference of a reception filter having a frequency property.

7. The ultrasonic diagnostic apparatus of claim 5,
wherein the processing circuitry is further configured to
detect a second Doppler signal from first ultrasonic reception IQ signals corresponding to a first group of channels, and to detect a third Doppler signal from second ultrasonic reception IQ signals corresponding to a second group of channels; and
calculate the blood flow velocity for each of the first, second, and third Doppler signals, respectively, and estimate the overall blood flow velocity as a weighted average of the calculated blood flow velocity for the first, second, and third Doppler signals.

* * * * *